United States Patent [19]

Lautenschläger et al.

[11] 4,349,684

[45] Sep. 14, 1982

[54] N-SUBSTITUTED ω-(2-OXO-4-IMIDAZOLIN-1-YL) ALCANOIC ACIDS AND SALTS AND ESTERS THEREOF

[75] Inventors: Hans-Heiner Lautenschläger, Pulheim-Stommeln; Hans Betzing, Kerpen-Horrem; Brigitte Stoll, Pulheim; Manfred Probst, Frechen, all of Fed. Rep. of Germany

[73] Assignee: A. Nattermann & Cie GmbH, Cologne, Fed. Rep. of Germany

[21] Appl. No.: 318,962

[22] Filed: Nov. 6, 1981

[30] Foreign Application Priority Data

Nov. 11, 1980 [DE] Fed. Rep. of Germany ....... 3042466

[51] Int. Cl.³ ............................................ C07D 233/70
[52] U.S. Cl. .................................... 548/320; 548/321
[58] Field of Search ............................. 548/320, 321

[56] References Cited

U.S. PATENT DOCUMENTS 3,905,996 9/1975 Perronnet et al. ................. 548/320

FOREIGN PATENT DOCUMENTS 42-186 1/1967 Japan.

Primary Examiner—Robert W. Ramsuer
Attorney, Agent, or Firm—Pearne, Gordon, Sessions, McCoy & Granger

[57] ABSTRACT

The present invention refers to N-substituted ω-(2-oxo-4-imidazolin-1-yl) alcanoic acids as well as salts and esters thereof having the general formula I

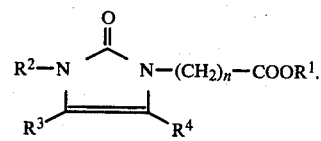

The compounds are useful, for example, as antiallergics, antiasthmatics, etc.

18 Claims, No Drawings

N-SUBSTITUTED ω-(2-OXO-4-IMIDAZOLIN-1-YL) ALCANOIC ACIDS AND SALTS AND ESTERS THEREOF

As described in two own prior, non-published German patent applications Nos. (P 29 34 746.4 and P 29 50 478.7), 5- and 4.5-substituted ω-(2-oxo-4-imidazolin-1-yl) alcanoic acids as well as their salts and esters have valuable pharmacological properties such as antithrombotic, antiarteriosklerotic, antiinflammatory and analgetic properties.

The present invention refers to new N-substituted ω-(2-oxo-4-imidazolin-1-yl) alcanoic acid derivatives having the general formula I

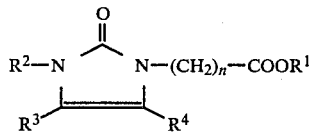

wherein
n is an integer ranging from 1 to 10, preferably ranging from 6 to 8,
$R^1$ represents hydrogen, an alkali metal ion or a straight or branched hydrocarbon group having from 1 to 6 carbon atoms or the benzyl group,
$R^2$ is $—(CH_2)_m—R$, m being 0, 1 or 2,
R, $R^3$ and $R^4$, which may be identical or different from each other, represent hydrogen (with the exception of R if m is zero), the unsubstituted phenyl group or the phenyl group substituted by one or several identical or differing substituents selected from the group consisting of halogen (in particular chlorine or fluorine), $CH_3—$, $CH_3O—$, $—CF_3$, at least one of R, $R^3$ and $R^4$ being a phenyl group or the phenyl group substituted by one or several identical or differing substituents selected from the group of halogen, $—CH_3$, $CH_3O—$, $—CF_3$.

The present invention further refers to processes for producing the same.

The new compounds show interesting pharmacological properties such as antiallergic, antiasthmatic, antithrombotic, antiarteriosklerotic and antiinflammatory properties. They furthermore show antagonistic activity in respect to some physiological processes regulated by PAF (platelet activation factor) as well as excellent compatibility by the stomach and may therefor in particular used for the treatment of thrombotic, allergic, asthmatic and arteriosclerotic as well as inflammatory deseases with at the same time favourable gastrointestinal properties. Furthermore, the compounds of formula I have a low toxicity. They furthermore may be produced in combination with anticoagulantia, in particular with heparin and heparinates.

The new N-substituted ω-(2-oxo-4-imidazolin-1-yl)alcanoic acid derivatives in the form of the free acids or of the salts thereof with pharmacologically compatible bases or as esters thereof may be used as active ingredient in drugs together with usual carrier materials or diluents.

The compounds of general formula I according to the present invention are used in dosages ranging from 0.1 to 100 mg/kg, in particular 1 to 50 mg/kg.

The compounds according to the present invention are produced according to the invention in that a 4-imidazolin-2-one of the general formula II

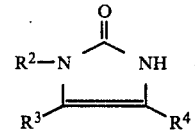

wherein $R^2$, $R^3$ and $R^4$ have the same meaning as in formula I, which may be produced by known processes usual in the chemistry of heterocyclic compounds from isocyanates and α-aminoketones or, respectively, from benzoketones with substituted ureas, is subjected to reaction with an alkylating agent of the general formula III $$X—(CH_2)_n—COOR^1 \qquad \text{III}$$

wherein n and $R^1$ have the same meaning as in formula I and X is a halogen atom, in an organic solvent such as acetone, methyl ethyl ketone, dimethylformamide with the addition of an auxiliary base such as sodium hydride, possibly in the presence of an alkali metal iodide as catalyst.

The resulting esters of formula I may converted into the corresponding alkali metal salt of formula I ($R^1$=alkali metal) in usual manner for instance by reaction with an alkali metal hydroxide in an aqueous, alcoholic or alcohol-ethereal solvent and by subsequent addition of a mineral acid into the acid of formula I ($R^1$=H).

In another way the acids of formula I ($R^1$=H) and the alkali metal salts thereof of formula I ($R^1$=alkali metal) may be converted into the esters of formula I ($R^1$=$C_{1-6}$-alkyl or benzyl) in manners usual in organic chemistry, for instance by the treatment of the compounds of formula I with a solution of hydrochloric acid in the corresponding alcohol or by subjecting the acid or the salt of formula I to reaction with thionyl chloride and subsequent reaction with the corresponding alcohol.

The compounds of formula I may also be produced by subjecting an ω-(2-oxo-4-imidazolin-1-yl)-alcanoic acid or a derivative thereof having the general formula IV

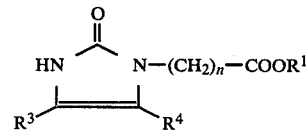

wherein $R^1$, $R^3$ and $R^4$ have the same meaning as in formula I, which may be produced by the synthesis described in the German patent application No. P 29 50 478.7, to reaction with an alkylating agent of formula V $$R^2\text{-Y} \qquad \text{V}$$

wherein Y has the same meaning of X in formula III or Y is another usual favourable group to be split off, for instance the $N_2$-group or the radical of a sulphuric acid ester, in particular of a sulphuric acid lower alkyl ester.

Substituted phenyl groups $R^2$ (or, respectively, R), $R^3$ and $R^4$ are for instance: 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2.5-dimethoxyphenyl, 3.4-dimethoxyphenyl, 3.4.5-trimethoxyphenyl, 2-methylphenyl, 3-methylphenyl, 4-methylphenyl, 2-trifluoromethylphenyl, 3-trifluoromethylphenyl, 4-trifluoromethylphenyl.

Alkylating agents of formula III are for instance the esters of the following ω-halogeno alcanoic acids:

chloroacetic acid, bromoacetic acid, iodoacetic acid, 3-chloropropionic acid, 3-bromopropionic acid, 3-iodopropionic acid, 4-chlorobutyric acid, 4-bromobutyric acid, 4-iodobutyric acid, 5-chlorovaleric acid, 5-bromovaleric acid, 5-iodovaleric acid, 6-chlorocapronic acid, 6-bromocapronic acid, 6-iodocapronic acid, 7-chloroenanthic acid, 7-bromoenanthic acid, 7-iodoenanthic acid, 8-chlorocaprylic acid, 8-bromocaprylic acid, 8-iodocaprylic acid, 9-chloropelargonic acid, 9-bromopelargonic acid, 9-iodopelargonic acid, 10-chlorocaprinic acid, 10-bromocaprinic acid, 10-iodocaprinic acid, 11-chloroundecanoic acid, 11-bromoundecanoic acid, 11-iodoundecanoic acid.

Examples for the alkylating agents of formula V are:
Diazomethane, dimethylsulfate, chloromethane, bromomethane, iodomethane, chloroethane, bromoethane, iodoethane, benzylchloride, benzylbromide, benzyliodide, phenylethylchloride, phenylethylbromide, phenylethyliodide as well as those substituted benzyl- and phenylethyl halogenides corresponding to R.

The alcohols $R^1OH$ preferably are such alcohols with straight or secondary branched saturated hydrocarbon groups with 1 to 6 carbon atoms such as methanol, ethanol, propanol, isopropanol, butanol, pentanol, hexanol as well as benzylalcohols.

The new compounds of formula I may be administered orally or by injection or rectally as suitable pharmaceutical products which may be solid or liquid, in the form of suspensions or solutions. Examples for such pharmaceutical products are tablets, powders, capsules, granules, ampoules, sirups and suppositories.

The production of the compounds according to the present invention are further illustrated in the following examples.

The given melting points have been determined on a BÜCHI 510 melting point determination apparatus and are not corrected. The IR-spektra have been determined on a PERKIN ELMER 257 and the mass spektra on a VARIAN MAT-311 A (70 eV).

EXAMPLE 1

[3-(4-Chlorophenyl)-2-oxo-4-phenyl-4-imidazolin-1-yl] acetic acid ethyl ester 1.5 g of sodium hydride (80% suspension in mineral oil) are washed with n-pentane and added to a mixture of 13.5 g 1-(4-chlorophenyl)-5-phenyl-4-imidazolin-2-one and 100 cc. of anhydrous dimethylformamide (DMF). The mixture is stirred at room temperature and heated to 60° C. with continuation of stirring towards the end of hydrogen formation. Thereafter, 6.2 g of chloroacetic acid ethyl ester and 1.5 g of sodiumiodide (NaJ) are added and the mixture is heated to 80° C. for 8 hours. After cooling, the reaction product is diluted with water, extracted with ether, the ether phase is washed consequetively with water, with 5% $NaHCO_3$ solution and again with water. The ethereal solution is dried over $Na_2SO_4$, the solvent is distilled off in a vacuum and the residue is purified chromatographically on silicic acid gel using chloroform as eluant.

Yield: 14.5 g. Fp. 96° to 97° C. IR (in KBr): 1755 and 1700 cm$^{-1}$.

EXAMPLE 2

7-[3-(4-Chlorophenyl)-2-oxo-4-phenyl-4-imidazolin-1-yl] enanthic acid ethyl ester The product is obtained as described in example 1 from 1.35 g NaJ (80% suspension in mineral oil), 12.2 g of 1-(4-chlorophenyl)-5-phenyl-4-imidazolin-2-one, 100 cc. of DMF, 8.7 g of 7-chloroenanthic acid ethyl ester and 1.35 g of NaJ. Eluant in chromatographic purification: hexane/ethyl acetate.

Yield: 15.7 g (oil) IR (film): 1735 and 1700 cm$^{-1}$.

EXAMPLE 3

7-(3-ethyl-4.5-diphenyl-2-oxo-4-imidazolin-1-yl) enanthic acid ethyl ester

The product is obtained as described in example 1 from 2.1 g of NaH (80% suspension in mineral oil), 18.5 g of 1-ethyl-4.5-diphenyl-4-imidazolin-2-one, 140 cc. of DMF, 13.5 g of 7-chloroenanthic acid ethyl ester and 2.1 g of NaJ.

Yield: 14.5 g (oil) IR (film): 1735 and 1690 cm$^{-1}$.

EXAMPLE 4

8-(3.4-Diphenyl-2-oxo-4-imidazolin-1-yl)-caprylic acid methyl ester

The product is produced as described in example 1 from 2.34 g of NaH (80% suspension in mineral oil), 18.5 g of 1.5-diphenyl-4-imidazolin-2-one, 160 cc. of DMF, 18.5 g of 8-bromocaprylic acid methyl ester and 2.34 g of NaJ.

Eluant in chromatographic purification: hexane/ethyl acetate.

Yield: 14 g, Fp. 45° to 47° C. IR (film): 1740 and 1695 cm$^{-1}$.

EXAMPLE 5

8-[3-(4-Chlorophenyl)-2-oxo-4-phenyl-4-imidazolin-1-yl] caprylic acid methyl ester The product is produced as described in example 1 from 2.4 g of NaH (80% suspension in mineral oil), 21.6 g of 1-(4-chlorophenyl)-5-phenyl-4-imidazolin-2-one, 160 cc. of DMF, 19.0 g of 8-bromocaprylic acid methyl ester and 2.4 g of NaJ.

Yield: 33 g (oil) IR (FILM): 1740 and 1700 cm$^{-1}$.

EXAMPLE 6

8-[2-Oxo-4-phenyl-3-(3-trifluoromethylphenyl)-4-imidazolin-1-yl] caprylic acid methyl ester The product is produced as described in example 1 from 1.41 g of NaH (80% suspension in mineral oil), 14.3 g of 5-phenyl-1-(3-trifluoromethylphenyl)-4-imidazolin-2-one, 100 cc. of DMF, 11.1 g of 8-bromocaprylic acid methyl ester and 1.41 g of NaJ.

Eluant in chromatographic purification: hexane/ethyl acetate.

Yield: 7.0 g (oil) IR (film): 1740 and 1700 cm$^{-1}$.

EXAMPLE 7

8-[3-(4-Methoxyphenyl)-2-oxo-4-phenyl-4-imidazolin-1-yl] caprylic acid methyl ester The product is produced as described in example 1 from 2.4 g of NaH (80% suspension in mineral oil), 21.3 g of 1-(4-methoxyphenyl)-5-phenyl-4-imidazolin-2-one, 160 cc. of DMF 19 g of 8-bromocaprylic acid methyl ester and 2.4 g of NaJ. Eluant in chromatographic purification: hexane/ethyl acetate.

Yield: 18.9 g (oil) IR (film) 1740 and 1695 cm$^{-1}$.

EXAMPLE 8

8-[3-(4-Methylphenyl)-2-oxo-4-phenyl-4-imidazolin-1-yl] caprylic acid methyl ester The product is produced as described in example 1 from 2.25 g of NaH (80% suspension in mineral oil), 18.7 g of 1-(4-methylphenyl)-5-phenyl-4-imidazolin-2-one, 150 cc. of DMF, 17.8 g of 8-bromocaprylic acid methyl ester and 2.25 g of NaJ.

Yield: 18.4 g (oil) IR (film): 1740 and 1695 cm$^{-1}$.

EXAMPLE 9

8-[3-(4-Fluorophenyl)-2-oxo-4-phenyl-4-imidazolin-1-yl] caprylic acid methyl ester The product is product as described in example 1 from 2.16 g of NaH (80% suspension in mineral oil), 18.3 g of 1-(4-Fluorophenyl)-5-phenyl-4-imidazolin-2-one, 150 cc. of DMF, 17.1 g of 8-bromocaprylic acid methyl ester and 2.16 g of NaJ.

Yield: 16.7 g (oil) IR (film): 1740 and 1700 cm$^{-1}$.

EXAMPLE 10

8-[4-(4-Chlorophenyl)-2-oxo-3-phenyl-4-imidazolin-1-yl] caprylic acid methyl ester The product is produced as described in example 1 from 1.05 g of NaH (80% suspension in mineral oil), 9.5 g of 5-(4-chlorophenyl)-1-phenyl-4-imidazolin-2-one, 70 cc. of DMF, 8.3 g of 8-bromocaprylic acid methyl ester and 1.05 g of NaJ.

Eluant in chromatographic purification: hexane/ethyl acetate.

Yield: 8.3 g, Fp. 83° to 84° C. IR (in KBr): 1740 and 1690 cm$^{-1}$.

EXAMPLE 11

8-(3-Benzyl-2-oxo-4-phenyl-4-imidazolin-1-yl) caprylic acid methyl ester

The product is produced as described in example 1 from 1.8 g of NaH (80% suspension in mineral oil), 15 g of 1-benzyl-5-phenyl-4-imidazolin-2-one, 120 cc. of DMF, 14.2 g of 8-bromocaprylic acid methyl ester and 1.8 g of NaJ.

Yield: 18.8 g (oil) IR (film): 1735 and 1685 cm$^{-1}$.

EXAMPLE 12

8-(2-Oxo-3.4.5-triphenyl-4-imidazolin-1-yl) caprylic acid methyl ester

The product is produced as described in example 1 from 1.2 g of NaH (80% suspension in mineral oil), 12 g of 1.4.5-triphenyl-4-imidazolin-2-one, 80 cc. of DMF, 9.5 g of 8-bromocaprylic acid methyl ester and 1.2 g of NaJ.

Yield: 12.9 g (oil) IR (film): 1740 and 1700 cm$^{-1}$.

EXAMPLE 13

8-[4.5-Bis-(2-fluorophenyl)-3-methyl-2-oxo-4-imidazolin-1-yl] caprylic acid methyl ester The product is produced as described in example 1 from 0.63 of NaH (80% suspension in mineral oil), 5.9 g of 4.5-bis-(2-fluorophenyl)-1-methyl-4-imidazolin-2-one, 40 cc. of DMF, 5.0 g of 8-bromo caprylic methyl ester and 0.63 g of NaJ.

Eluant in chromatographic purification: hexane/ethyl acetate.

Yield: 5.3 g (oil) IR (film): 1740 and 1695 cm$^{-1}$.

EXAMPLE 14

8-(4.5-Diphenyl-3-methyl-2-oxo-4-imidazolin-1-yl) caprylic acid methyl ester

The product is produced as described in example 1 from 2.4 g of NaH (80% suspension in mineral oil), 20 g of 4.5-diphenyl-1-methyl-4-imidazolin-2-one, 160 cc. of DMF, 19 g of 8-bromocaprylic acid methyl ester and 2.4 g of NaJ.

Eluant in chromatographic purification: hexane/ethyl acetate.

Yield: 17.5 g (oil) IR (film): 1740 and 1690 cm$^{-1}$.

EXAMPLE 15

9-[3-(4-Chlorophenyl)-2-oxo-4-phenyl-4-imidazolin-1-yl] pelargonic acid methyl ester The product is produced as described in example 1 from 1.35 g of NaH (80% suspension in mineral oil), 12.2 g of 1-(4-chlorophenyl)-5-phenyl-4-imidazolin-2-one, 90 cc. of DMF, 11.3 g of 9-bromo-nonanic acid methyl ester and 1.35 g of NaJ.

Eluant in chromatographic purification: hexane/ethyl acetate.

Yield: 5.4 g, Fp. 54° to 56° C. IR (in KBr): 1740 and 1690 cm$^{-1}$.

EXAMPLE 16

11-(3-ethyl-4.5-diphenyl-2-oxo-4-imidazolin-1-yl) undecanoic acid methyl ester

The product is produced as described in example 1 from 0.45 g of NaH (80% suspension in mineral oil), 4 g of 1-ethyl-4.5-diphenyl-4-imidazolin-2-one, 30 cc. of DMF, 4.2 g of 11-bromoundecanoic acid methyl ester and 0.45 g of NaJ.

Eluant in chromatographic purification: hexane/ethyl acetate.

Yield: 1.5 g (oil) IR (film): 1740 and 1690 cm$^{-1}$.

EXAMPLE 17

8-(3-Methyl-2-oxo-5-phenyl-4-imidazolin-1-yl) caprylic acid 3.2 g of 8-(2-oxo-5-phenyl-4-imidazolin-1-yl) caprylic acid sodium salt (preparation see German patent application No. P 29 34 746.4) are suspended in 20 cc. of acetone together with 2.8 g of pulverized potassium hydroxide. The mixture is refluxed and converted into a homogenous solution by the addition of some drops of water. Thereafter, 2.8 g of methyliodide are added at boiling temperature, the mixture is refluxed for 30 minutes and cooled to room temperature. After cooling, so much of water is added that precipitated solids are dissolved. The solution is stirred at room temperature for 4 hours, is acidified and diluted with water until the crude acid is separated as oil. The oil is dissolved in a small amount of chloroform, the chloroform phase is washed with water several times and is finally extracted with 5% soda lye. The soda lye extract is washed with chloroform, the aqueous solution is acidified with dilute hydrochloric acid and is separated from the acid precipitated as an oil. Purification occurs by chromatography on silicic acid gel using a mixture of chloroform and methanol as eluant.

Yield: 2.6 g (oil)

MS (m/e): 316 (100%), 187 (29%), 174 (65%), 159 (4.8%), 105 (7.7%).

EXAMPLE 18

[3-(4-Chlorophenyl)-2-oxo-4-phenyl-4-imidazolin-1-yl] acetic acid 13.6 g of [3-(4-chlorophenyl)-2-oxo-4-phenyl-4-imidazolin-1-yl] acetic acid ethyl ester and 1.52 g of NaOH are dissolved in 80 cc. of ethanol and the mixture is stirred at room temperature for 24 hours. The alcohol is distilled off in a vacuum and the residue is dissolved in water. The aqueous solution is shaken with ether, the aqueous phase is acidified with dilute hydrochloric acid and the precipitated acid is separated and dried.

Yield: 6.0 g, Fp. 214° to 215° C.

MS (m/e): 328 (100%), 284 (30%), 269 (2.5%), 214 (14%).

EXAMPLE 19

7-[3-(4-Chlorophenyl-2-oxo-4-phenyl-4-imidazolin-1-yl] enanthic acid

The product is produced as described in example 18 from 13.5 g of 7-[3-(4-chlorophenyl)-2-oxo-4-phenyl-4-imidazolin-1-yl] enanthic acid ethel ester, 1.28 g of NaOH in 60 cc. of ethanol.

Yield: 10.0 g, Fp. 141° C.

MS (m/e): 398 (100%), 284 (17%), 270 (27%), 214 (22%).

EXAMPLE 20

7-(3-Ethyl-4.5-diphenyl-2-oxo-4-imidazolin-1-yl) enanthic acid

The product is produced as described in example 18 from 12.3 g of 7-(3-ethyl-4.5-diphenyl-2-oxo-4-imidazolin-1-yl) enanthic acid ethyl ester and 1.16 g of NaOH in 60 cc. of ethanol. Further purification by chromatography on silicic acid gel using chloroform as eluant.

Yield: 4.2 g, Fp. 111° to 112° C.

MS (m/e): 392 (100%), 277 (8%), 264 (18%), 104 (6%).

EXAMPLE 21

8-(3.4-Diphenyl-2-oxo-4-imidazolin-1-yl) caprylic acid

The product is produced as described in example 18 from 8.2 g of 8-(3.4-diphenyl-2-oxo-4-imidazolin-1-yl) caprylic acid methyl ester and 0.84 g of NaOH in 20 cc. of ethanol. Further purification by chromatography on silicic acid gel using chloroform as eluant.

Yield: 1.4 g, Fp. 108° C.

MS (m/e): 378 (100%), 249 (20%), 236 (26%), 180 (24%).

EXAMPLE 22

8-[3-(4-Chlorophenyl)-2-oxo-4-phenyl-4-imidazolin-1-yl] caprylic acid

The product is produced as described in example 18 from 20 g of 8-[3-(4-chlorophenyl)-2-oxo-4-phenyl-4-imidazolin-1-yl] caprylic acid methyl ester and 1.88 g of NaOH in 100 cc. of methanol. Further purification by chromatography on silicic acid gel using a mixture of hexane annd ethyl acetate as eluant.

Yield: 8.5 g, Fp. 100° to 101° C.

MS (m/e): 412 (100%), 284 (11%), 270 (18%), 214 (16%).

EXAMPLE 23

8-[2-Oxo-4-phenyl-3-(3-trifluoromethyl-phenyl)-4-imidazolin-1-yl] caprylic acid

The product is produced as described in example 18 from 6.9 g of 8-[2-oxo-4-phenyl-3-(3-trifluoromethyl-phenyl)-4-imidazolin-1-yl] caprylic acid methyl ester and 0.66 g of NaOH in 30 cc. of methanol. Further purification by chromatography on silicic acid gel using chloroform as eluant.

Yield: 4.55 g, Fp. 113° to 114° C.

MS (m/e): 466 (100%), 318 (10%), 304 (21%), 248 (14%).

EXAMPLE 24

8-[3-(4-Methoxyphenyl)-2-oxo-4-phenyl-4-imidazolin-1-yl] caprylic acid

The product is produced as described in example 18 from 18.8 g of 8-[3-(4-methoxyphenyl)-2-oxo-4-phenyl-4-imidazolin-1-yl] caprylic acid methyl ester and 2.12 g of NaOH in 100 cc. of methanol. Further purification by chromatography on silicic acid gel using chloroform as eluant.

Yield: 6.6 g, Fp. 110° C.

MS (m/e): 408 (100%), 279 (14%), 266 (18%), 210 (26%).

EXAMPLE 25

8-[3-(4-Methylphenyl)-2-oxo-4-phenyl-4-imidazolin-1-yl] caprylic acid

The product is produced as described in example 18 from 18.1 g of 8-[3-(4-methylphenyl)-2-oxo-4-phenyl-4-imidazolin-1-yl] caprylic acid methyl ester and 1.8 g of NaOH in 90 cc. of methanol. Further purification by chromatography on silicic acid gel using chloroform as eluant.

Yield: 6.6 g, Fp. 110° to 101° C.

MS (m/e): 392 (100%), 264 (11%), 250 (14%), 194 (12%).

EXAMPLE 26

8-[3-(4-Fluorophenyl)-2-oxo-4-phenyl-4-imidazolin-1-yl] caprylic acid

The product is produced as described in example 18 from 16.4 g of 8-[3-(4-fluorophenyl)-2-oxo-4-phenyl-4-imidazolin-1-yl] caprylic acid methyl ester and 1.6 g of NaOH in 80 cc. of methanol. Further purification by chromatography on silicic acid gel using chloroform as eluant.

Yield: 3.6 g, Fp. 110° C.

M/S (m/e): 396 (100%), 268 (11%), 254 (18%), 198 (16%).

EXAMPLE 27

8-[4-(4-Chlorophenyl)-2-oxo-4-phenyl-4-imidazolin-1-yl] caprylic acid

The product is produced as described in example 18 from 6.1 g of 8-[4-(4-chlorophenyl)-2-oxo-3-phenyl-4-imidazolin-1-yl] caprylic acid ethyl ester and 0.56 g of NaOH in 30 cc. of methanol. The product is finally boiled in a small amount of ether, filtered off with suction and dried.

Yield: 3.6 g, Fp. 156° to 157° C.

MS (m/e): 412 (100%), 284(14%), 270 (23%), 214 (16%).

EXAMPLE 28

8-(3-Benzyl-2-oxo-4-phenyl-4-imidazolin-1-yl) caprylic acid

The product is produced as described in example 18 from 20.3 g of 8-(3-benzyl-2-oxo-4-phenyl-4-imidazolin-1-yl) caprylic acid methyl ester. Further purification by chromatography on silicic acid gel using chloroform as eluant.

Yield: 9.5 g, Fp. 95° C.

MS (m/e): 392 (82%), 173 (13%), 159 (10%), 91 (100%).

EXAMPLE 29

8-(2-Oxo-3.4.5-triphenyl-4-imidazolin-1-yl)-caprylic acid

The product is prepared as described in example 18 from 7.5 g of 8-(2-oxo-3.4.5-triphenyl-4-imidazolin-1-yl)-caprylic acid methyl ester and 0.64 g of NaOH in 30 cc. of methanol. Further purification by chromatography on silicic acid gel using chloroform as eluant.

Yield: 3.5 g, Fp. 142° to 143° C.

MS (m/e): 454 (100%), 325 (14%), 312 (23%), 180 (11%).

EXAMPLE 30

8-[4.5-Bis-(2-fluorophenyl)-3-methyl-2-oxo-4-imidazolin-1-yl] caprylic acid

The product is produced as described in example 18 from 5.2 g of 8-[4.5-bis-(2-fluorophenyl)-3-methyl-2-oxo-4-imidazolin-1-yl] caprylic acid methyl ester and 0.53 g of NaOH in 25 cc. of methanol. Recrystallization from ether/hexane.

Yield: 3.9 g, Fp. 130° to 131° C.

MS (m/e): 428 (100%), 299 (24%), 286 (53%).

EXAMPLE 31

8-(4.5-Diphenyl-3-methyl-2-oxo-4-imidazolin-1-yl) caprylic acid

The product is produced as described in example 18 from 17.5 g of 8-(4.5-diphenyl-3-methyl-2-oxo-4-imidazolin-1-yl) caprylic acid methyl ester and 2.1 g of NaOH in 100 cc. of methanol. Further purification by chromatography on silicic acid gel using chloroform as eluant.

Yield: 10.2 g, Fp. 112° to 114° C.

MS (m/e): 392 (100%), 263 (10%), 250 (33%).

EXAMPLE 32

9-[3-(4-Chlorophenyl)-2-oxo-4-phenyl-4-imidazolin-1-yl] pelargonic acid

The product is produced as described in example 18 from 4.4 g of 9-[3-(4-chlorophenyl)-2-oxo-4-phenyl-4-imidazolin-1-yl] pelargonic acid methyl ester and 0.4 g of NaOH in 20 cc. of methanol. Further purification by chromatography on silicic acid gel using chloroform as eluant.

Yield: 2.8 g, Fp. 143° to 144° C.

MS (m/e): 426 (100%), 284 (11%), 270 (20%), 214 (17%).

EXAMPLE 33

[3-(4-Chlorophenyl)-2-oxo-4-phenyl-4-imidazolin-1-yl] acetic acid sodium salt 5 g of [3-(4-chlorophenyl)-2-oxo-4-phenyl-4-imidazolin-1-yl] acetic acid are dissolved in ethanol, the solution is neutralized with the equivalent amount of alcoholic soda lye and the resulting solution is evaporated to dryness in a vacuum. The solid residue is pulverized.

Yield: 100% IR (in KBr): 1675 and 1600 cm$^{-1}$.

As described in example 33, examples 34 to 47 (see table 1) have been executed.

TABLE 1

Sodium salt of N-substituted ω-(2-oxo-4-imidazolin-1-yl) alcanoic acids $$R^2-N-\overset{\overset{O}{\|}}{C}-N-(CH_2)_n-COOR^1$$
$$R^3 \quad R^4$$

| Example No. | $R^1$ | $R^2$ | $R^3$ | $R^4$ | n | IR maxima in KBr in cm$^{-1}$ | corresponding acid |
|---|---|---|---|---|---|---|---|
| 34 | Na | Cl—⌬— | —⌬ | H | 6 | 1690, 1570 | 7-[3-(4-Chlorophenyl)-2-oxo-4-phenyl-4-imidazolin-1-yl] enanthic acid |
| 35 | Na | C$_2$H$_5$ | —⌬ | —⌬ | 6 | 1690, 1575 | 7-(3-Ethyl-4.5-diphenyl-2-oxo-4-imidazolin-1-yl) enanthic acid |
| 36 | Na | —⌬ | —⌬ | H | 7 | 1690, 1570 | 8-(3.4-Diphenyl-2-oxo-4-imidazolin-1-yl) caprylic acid |
| 37 | Na | Cl—⌬— | —⌬ | H | 7 | 1690, 1570 | 8-[3-(4-Chlorophenyl)-2-oxo-4-phenyl-4-imidazolin-1-yl] caprylic acid |
| 38 | Na | CF$_3$—⌬ | —⌬ | H | 7 | 1695, 1570 | 8-[2-Oxo-4-phenyl-3-(3-trifluoromethylphenyl)-4-imidazolin-1-yl] caprylic acid |
| 39 | Na | CH$_3$O—⌬— | —⌬ | H | 7 | 1690, 1570 | 8-[3-(4-Methoxyphenyl)-2-oxo-4-phenyl-4-imidazolin-1-yl] caprylic acid |

TABLE 1-continued

Sodium salt of N-substituted ω-(2-oxo-4-imidazolin-1-yl) alcanoic acids $$R^2-N \underset{R^3 \diagup\!\!=\!\!\diagdown R^4}{\overset{\overset{O}{\|}}{\diagup\!\!\diagdown}} N-(CH_2)_n-COOR^1$$

| Example No. | R¹ | R² | R³ | R⁴ | n | IR maxima in KBr in cm⁻¹ | corresponding acid |
|---|---|---|---|---|---|---|---|
| 40 | Na | CH₃—⌬— | ⌬— | H | 7 | 1690, 1570 | 8-[3-(4-Methylphenyl)-2-oxo-4-phenyl-4-imidazolin-1-yl] caprylic acid |
| 41 | Na | F—⌬— | ⌬— | H | 7 | 1690, 1570 | 8-[3-(4-Fluorophenyl)-2-oxo-4-phenyl-4-imidazolin-1-yl] caprylic acid |
| 42 | Na | ⌬— | Cl—⌬— | H | 7 | 1685, 1565 | 8-[4-(4-Chlorophenyl)-2-oxo-3-phenyl-4-imidazolin-1-yl] caprylic acid |
| 43 | Na | ⌬—CH₂— | ⌬— | H | 7 | 1690, 1570 | 8-(3-Benzyl-2-oxo-4-phenyl-4-imidazolin-1-yl) caprylic acid |
| 44 | Na | ⌬— | ⌬— | ⌬— | 7 | 1700, 1565 | 8-(2-Oxo-3,4,5-triphenyl-4-imidazolin-1-yl)-caprylic acid |
| 45 | Na | CH₃— | ⌬(F)— | ⌬(F)— | 7 | 1690, 1570 | 8-[4,5-Bis-(2-fluorophenyl)-3-methyl-2-oxo-4-imidazolin-1-yl] caprylic acid |
| 46 | Na | CH₃— | ⌬— | ⌬— | 7 | 1690, 1570 | 8-(4,5-Diphenyl-3-methyl-2-oxo-4-imidazolin-1-yl) caprylic acid |
| 47 | Na | Cl—⌬— | ⌬— | H | 8 | 1695, 1570 | 9-[3-(4-Chlorophenyl)-2-oxo-4-phenyl-4-imidazolin-1-yl] pelargonic acid |

EXAMPLE 48

[3-(4-Chlorophenyl)-2-oxo-4-phenyl-4-imidazolin-1-yl] acetic acid hexyl ester 1 g of [3-(4-chlorophenyl)-2-oxo-4-phenyl-4-imidazolin-1-yl] acetic acid are dissolved in a small amount of anhydrous chloroform. 0.7 g of thionylchloride are added thereto and the mixture is stirred at about 50° C. for 2 hours. The mixture is evaporated in a vacuum, the residue is mixed with a small amount of chloroform and 0.31 g of hexanol are added to the mixture. After stirring for one hour at room temperature, the CHCl₃-solution is first extracted with an NaHCO₃-solution and then with water. It finally is dried over Na₂SO₄. The CHCl₃-solution is evaporated, remaining hexanol is distilled off a high vacuum and the residue is further purified chromatographically on silicic acid gel using CHCl₃ as eluant.

Yield: 0.5 g (oil)
IR (film): 1750 and 1710 cm⁻¹.

EXAMPLE 49

8-(4,5-Diphenyl-3-methyl-2-oxo-4-imidazolin-1-yl) caprylic acid benzyl ester

The product is prepared as described in Example 48 from 1.5 g of 8-(4,5-diphenyl-3-methyl-2-oxo-4-midazolin-1-yl) caprylic acid, 0.55 g of thionyl chloride and 0.37 g of benzyl alcohol.

Yield: 1.4 g (oil)

IR (film: 1740 and 1700 cm⁻¹.

What we claim is:

1. N-substituted ω-(2-oxo-4-imidazolin-1-yl) alcanoic acids and their derivatives having the general formula I

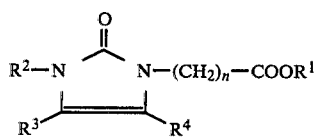

wherein
n is an integer from 1 to 10,
R¹ is hydrogen, an alkali metal ion or a straight or branched hydrocarbon group having from 1 to 6 carbon atoms or the benzyl group,
R² is —(CH₂)ₘ—R wherein m is 0, 1 or 2,
R, R³ and R⁴ which may be identical or different from each other, represent hydrogen (with the exception of R if m is zero), the unsubstituted phenyl group or the phenyl group substituted by one or several equal or differing substituents selected from the group of halogen, CH₃—, CH₃O—, —CF₃, at least one of R, R³ and R⁴ representing the unsubstituted phenyl or the phenyl group substituted by one or several identical or differing substituents selected from the group of halogen, —CH₃, CH₃O—, —CF₃.

2. [3-(4-Chlorophenyl)-2-oxo-4-phenyl-4-imidazolin-1-yl] acetic acid and the pharmaceutically compatible salts and esters thereof.

3. 7-[3-(4-Chlorophenyl)-2-oxo-4-phenyl-4-imidazolin-1-yl] enanthic acid and the pharmaceutically compatible salts and esters thereof.

4. 7-(3-ethyl-4.5-diphenyl-2-oxo-4-imidazolin-1-yl) enanthic acid and the pharmaceutically compatible salts and esters thereof.

5. 8-(3.4-Diphenyl-2-oxo-4-imidazolin-1-yl) caprylic acid and the pharmaceutically compatible salts and esters thereof.

6. 8-[3-(4-Chlorophenyl)-2-oxo-4-phenyl-4-imidazolin-1-yl] caprylic acid and the pharmaceutically compatible salts and esters thereof.

7. 8-[2-Oxo-4-phenyl-3-(3-trifluoromethyl-phenyl)-4-imidazolin-1-yl] caprylic acid and the pharmaceutically compatible salts and esters thereof.

8. 8-[3-(4-Methoxyphenyl)-2-oxo-4-phenyl-4-imidazolin-1-yl] caprylic acid and the pharmaceutically compatible salts and esters thereof.

9. 8-[3-(4-Methylphenyl)-2-oxo-4-phenyl-4-imidazolin-1-yl] caprylic acid and the pharmaceutically compatible salts and esters thereof.

10. 8-[3-(4-Fluorophenyl)-2-oxo-4-phenyl-4-imidazolin-1-yl] caprylic acid und the pharmaceutically compatible salts and esters thereof.

11. 8-[4-(4-Chlorophenyl)-2-oxo-3-phenyl-4-imidazolin-1-yl] caprylic acid and the pharmaceutically compatible salts and esters thereof.

12. 8-(3-Benzyl-2-oxo-4-phenyl-4-imidazolin-1-yl) caprylic acid and the pharmaceutically compatible salts and esters thereof.

13. 8-(2-Oxo-3.4.5-triphenyl-4-imidazolin-1-yl)caprylic acid and the pharmaceutically compatible salts and esters thereof.

14. 8-[4.5-Bis-(2-fluorophenyl)-3-methyl-2-oxo-4-imidazolin-1-yl] caprylic acid and the pharmaceutically compatible salts and esters thereof.

15. 8-(4.5-Diphenyl-3-methyl-2-oxo-4-imidazolin-1-yl) caprylic acid and the pharmaceutically compatible salts and esters thereof.

16. 8-(3-Methyl-2-oxo-5-phenyl-4-imidazolin-1-yl) caprylic acid und the pharmaceutically compatible salts and esters thereof.

17. 9-[3-(4-Chlorophenyl)-2-oxo-4-phenyl-4-imidazolin-1-yl] pelargonic acid and the pharmaceutically compatible salts and esters thereof.

18. 11-(3-Ethyl-4.5-diphenyl-2-oxo-4-imidazolin-1-yl) undecanoic acid and the pharmaceutically compatible salts and esters thereof.

* * * * *